US006329652B1

(12) United States Patent
Windig et al.

(10) Patent No.: US 6,329,652 B1
(45) Date of Patent: Dec. 11, 2001

(54) METHOD FOR COMPARISON OF SIMILAR SAMPLES IN LIQUID CHROMATOGRAPHY/ MASS SPECTROMETRY

(75) Inventors: Willem Windig, Rochester; William F. Smith, Brockport, both of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/362,639

(22) Filed: Jul. 28, 1999

(51) Int. Cl.$^7$ ........................................................ H01J 49/00
(52) U.S. Cl. ........................... 250/282; 250/288; 73/23.2; 73/23.37; 73/23.36
(58) Field of Search .................................... 250/282, 288, 250/288 A; 73/23.2, 23.37, 23.36; 702/19, 22–23, 27, 30, 32; 436/161, 173

(56) References Cited

U.S. PATENT DOCUMENTS

| 5,453,613 | * | 9/1995 | Gray et al. | 250/281 |
| 5,672,869 | | 9/1997 | Windig et al. . | |
| 6,147,344 | * | 11/2000 | Annis et al. | 250/281 |

OTHER PUBLICATIONS

Combined Liquid Chromatography Mass Spectrometry. Part III. Applications of Thermospray. P Arpino (1992) Mass Spectro. Review 11,3–40.

Thermospray interface for Liquid Chromatography/Mass Spectrometry, C.R. Blakely and M.L. Vestal (1983) Anal. Chem.55, 750–754.

Electrospray ionization–principles and practice. John B. Fenn, M Mann, CK Meng, SF Wong, CM Whitehouse, Mass Spectrometry Reviews 1990–9, 37–70.

Automatic extraction of relevant peaks and reconstruction of mass spectra for low signal–to–noise GC–MS data. Brahim El Abbassi et al, Int. J. Mass Spectr. Ion. Proc., 141 (1995) pp. 171–186.

Noise reduction of gas chromatography/Mass Spectrometry data using principal component analysis, T A Lee et al, Anal. Chem., 63 (1991) 357–360.

* cited by examiner

Primary Examiner—Kiet T. Nguyen
Assistant Examiner—Sharon Payne
(74) Attorney, Agent, or Firm—Mark G. Bocchetti

(57) ABSTRACT

A method is disclosed to reduce the time needed to analyze data generated from very similar samples, emphasizing the differences obtained, from the combined technique of liquid chromatography/mass spectrometry, a technique used to analyze the composition of materials. The method quickly compares each mass chromatogram between similar samples and displays the limited number of mass chromatograms that are different to the analyst.

8 Claims, 8 Drawing Sheets

METHOD FOR COMPARISON OF SIMILAR SAMPLES IN LIQUID CHROMATOGRAPHY/ MASS SPECTROMETRY

FIELD OF THE INVENTION

This invention relates to a method to reduce the noise, reduce the background and enhance the differences of total ion chromatograms obtained from highly similar materials using the combined technique of chromatography and mass spectrometry, which is a technique used to analyze the composition of materials. The method greatly improves the efficiency of the detection of the components that are different in highly similar materials.

BACKGROUND OF THE INVENTION

The invention illustrated herein relates to the combined technique of liquid chromatography (LC)/mass spectrometry (MS) (see for example: Arpino, P. (1992), Mass Spectrom. Rev.,11,3; Blakley, C. R., and Vestal, M. L. (1983), Anal. Chem.,55,750; J. B. Fenn,. M Mann,. C. K. Meng, S. F. Wong, C. M. Whitehouse, Mass Spectrometry Reviews, 1990, 9, 37–70; *Liquid Chromatography-Mass Spectrometry*: Second Edition, Volume 79, by W. M. A. Niessen, pgs. 135–344 but is also suited for other hyphenated techniques (e.g. gas chromatography/mass spectrometry, liquid chromatography/ultra violet spectroscopy, liquid chromatography/nuclear magnetic resonance spectroscopy). It will also be suitable for other time-resolved spectroscopic techniques, such as direct probe mass spectrometry, laser analysis for spectrometry, fast atom bombardment mass spectrometry. In the case presented for example, the LC is used to separate mixtures into individual components which are in turn passed through to the MS where mass spectral information is obtained on each component. Two or more samples of the same or very similar materials are analyzed under the same conditions. The mass spectral information is used both as a component detection system, and may also be used to characterize the molecular structure of the detected components.

Liquid chromatography itself, is one type of chromatographic technique. Chromatography is a method for separating mixtures. In the simplest application of a chromatographic process, a vertical tube is filled with a finely divided solid known as the stationary phase. The mixture of materials to be separated is placed at the top of the tube and is slowly washed down with a suitable liquid, or eluent, known as the mobile phase.

The mixture first dissolves, each molecule is transported in the flowing liquid, and then becomes attached, or adsorbed, to the stationary solid. Each type of molecule will spend a different amount of time in the liquid phase, depending on its tendency to be adsorbed, so each compound will descend through the tube at a different rate, thus separating from every other compound.

The molecules of the mixture to be separated pass many times between the mobile and stationary phases. The rate at which they do so depends on the mobility of the molecules, the temperature, and the binding forces involved. It is the difference in the time that each type of molecule spends in the mobile phase that leads to a difference in the transport velocity and to the separation of substances. (See FIG. 1a.)

High Pressure Liquid chromatography (HPLC), is a refinement of standard column chromatography. Here, the particles that carry the stationary liquid phase are very small (0.01 mm/0.0004 in) and very uniform in size. For these reasons, the stationary phase offers a large surface area to the sample molecules in the mobile liquid phase. The large pressure drop created in the column filled with such small particles is overcome by using a high-pressure pump to drive the mobile liquid phase through the column in a reasonable time. This method of separation is very reproducible from sample to sample.

Chromatography is used primarily as a separation technique. Despite the reproducible differences in the analysis times for different species noted above, there is generally insufficient specificity to allow identification of the components. For this reason, it is common for chromatographic techniques to be used in tandem with an identification technique, the technique most suitable and most often used being mass spectrometry.

The mass spectrum of a component generally provides a measure of the molecular weight of the component and also provides a characteristic 'fingerprint' fragmentation pattern. In a mass spectrometer, the component molecules become ionized and will be excited with a range of energies. Those molecules with least energy generally remain intact and when detected provide a measure of the component's molecular weight. Those molecules ionized with higher amounts of energy will fragment to form smaller product ions characteristic of the molecular structure. To obtain the molecular structure, the fragment ions produced can be pieced together to provide the initial molecular structure. An alternative method for obtaining the molecular structure from the mass spectrum is to compare the spectrum of the component with a large library of reference mass spectra. The unique nature of a component's mass spectrum generally allows ready and unequivocal identification if there is an example of the mass spectrum of that component in the reference library.

For LCMS, the chromatographic device then is interfaced directly to a mass spectrometer which is scanned repetitively (e.g. every 1–5 sec.) as the separated components elute from the chromatograph. In this way a large number of mass spectra are recorded for each analysis. Many of the spectra will record only 'background', i.e. when no components are eluting from the chromatograph. As each component elutes from the chromatograph, the mass spectra will change depending on the nature of the component entering the mass spectrometer. Each mass spectrum produced will contain a certain number of ions, which in turn give rise to an ion current which is plotted against time to produce a total ion chromatogram (TIC)).

An alternative plot is that of an individual mass against time to produce a mass chromatogram which will show just where that particular mass is detected during the analysis. For samples with UV chromophores, an in-line UV detector can be used to detect peaks. Knowing the peak retention times, the corresponding mass spectra can then be obtained. This indirect peak detection method is clearly limited to components with chromophores, which is a serious limitation.

In liquid chromatography/mass spectrometry (LCMS), most of the liquid mobile phase must be removed in the interface region prior to entering the mass spectrometer as mass spectrometers need to operate under high vacuum (See FIG. 1b). However, the liquid mobile phase is present in such excess that the mobile phase is still present in excess to analyte species even after passage through the interface. To obtain good component separations and clean passage of components through a LC column, it is also generally necessary to add buffers to the mobile phase. Hence, mobile phase with associated buffer pass continually through to the mass spectrometer, become ionized and are the major species responsible for the 'background' spectra referred to above. Unfortunately, particularly for the popular 'spray' LCMS interfacing and ionizing techniques (e.g. electrospray, thermospray), this background varies considerably with time and cannot just be subtracted from analyte spectra. This causes the small to medium level components in the separation to be lost in the high background noise response seen in the TIC.

A flow diagram of a LC-MS experiment is presented (FIG. 2).

The analysis of LC/MS data is a very time consuming and complex process. The intrinsic high background makes it difficult to pick out the lower level components in a mixture. CODA, previously described (U.S. Pat. No. 5,672,869), deals with the chemical noise and provides a high quality, low background data set containing the significant components detected in the sample. Comparison of very similar samples presents further challenges. Even with the use of CODA, it is difficult to see differences between related samples, unless the differences are major components. The problems are illustrated in FIG. 3. The chromatograms of three slightly different samples are shown. Despite the use of CODA, which reduces the number of chromatograms in each file from around 2000 to around 150, the minor differences between the samples are not clear. The separate evaluation of files, which is the only option with commercially available software, is a time consuming task, even after the significant data reduction by CODA.

A new method is needed to extract the differences between two or more closely related samples in order to obtain a faster analysis.

SUMMARY OF THE INVENTION

The present invention provides a solution to the problems described above. COMPARELCMS is a method specifically designed to highlight the differences between similar samples. Individual mass chromatograms for each ion are compared between the samples of choice, using certain rules. The similar mass chromatograms are discarded while the different mass chromatograms, as determined by the rules, are displayed to the analyst for examination. This greatly reduces the time commitment for examining similar samples.

In order to make the task of comparing the data manageable, the data are reduced in the following two ways:

a) Reduction of the number of mass chromatograms for each file separately.

This is achieved by first using CODA, or another system which reduces the number of mass chromatograms significantly such as the method developed by Abbassi et. al. (B. E. Abbassi, H. Mestdagh and C. Rolando, Int. J. Mass Spectr. Ion. Proc., 141 (1995) 171–186) or by just reducing noise by using principal components analysis (T. A. Lee, L. M. Headly and J. K. Hardy, Anal. Chem., 63 (1991) 357–360) and generally starts with a first step of subjecting said organic material to chromatography to separate components of said mixture and a second step of subjecting the separated materials to spectrometry to detect and identify said components, wherein said chromatography and spectrometry is performed by a) injecting a sample into a column;
b) separating components by partitioning at different rates in the column;
c) passing separated components into a spectrometer;
d) obtaining a series of spectra to detect all species present; and e) storing the spectra in a computer file and reducing the number of mass chromatograms; the improvement comprising enhancing the spectral data by a variable selection using the following steps: The CODA system continues with i) smoothing the spectroscopic variables;
ii) obtaining the mean value of the intensity of the spectroscopic variables;
iii) subtracting the mean value obtained in step i;
iv) normalizing the output of step iii and the original spectroscopic variables;
v) comparing the values of step iv to obtain a measure of similarity for each spectroscopic variable;
vi) determining a threshold value of similarity measurement so as to reject unwanted signals;
vii) selecting only those spectroscopic variables whose similarity measurement is over the threshold value; and
viii) plotting the sum of the selected variables versus time to obtain the enhanced chromatogram.

For the further processing, all the mass chromatograms selected are considered. For example, if m/e 151 was selected by CODA in only one file, m/e 151 of the other files will also be considered in the process. This selection is called combined CODA data reduction, After the combined CODA data reduction, a further data reduction is achieved by selecting mass chromatograms above a certain level in order to avoid noise and peaks that are very broad, and generally of no interest to the problem solving, and they are also discarded. This results in an additional data reduction.

Reduction of the number of mass chromatograms by selecting mass chromatograms that behave dissimilar between the files.

In order for a selected mass chromatogram to be marked as different, there needs to be a user defined minimum difference in the scan position of two of the chromatograms or the ratio between intensities of peaks exceeds a user-defined limit.

This results in an additional data reduction. In summary, the researcher is presented with a small fraction of the variables he would have to study with conventional means.

Furthermore, this invention enables the researcher to examine the chromatograms of the files simultaneously, instead of separately as by conventional tools. Because of this, the time consuming manual analysis of related samples is typically reduced from 4–8 hrs. to 5 minutes.

DETAILED DESCRIPTION OF THE INVENTION

Figure 4:
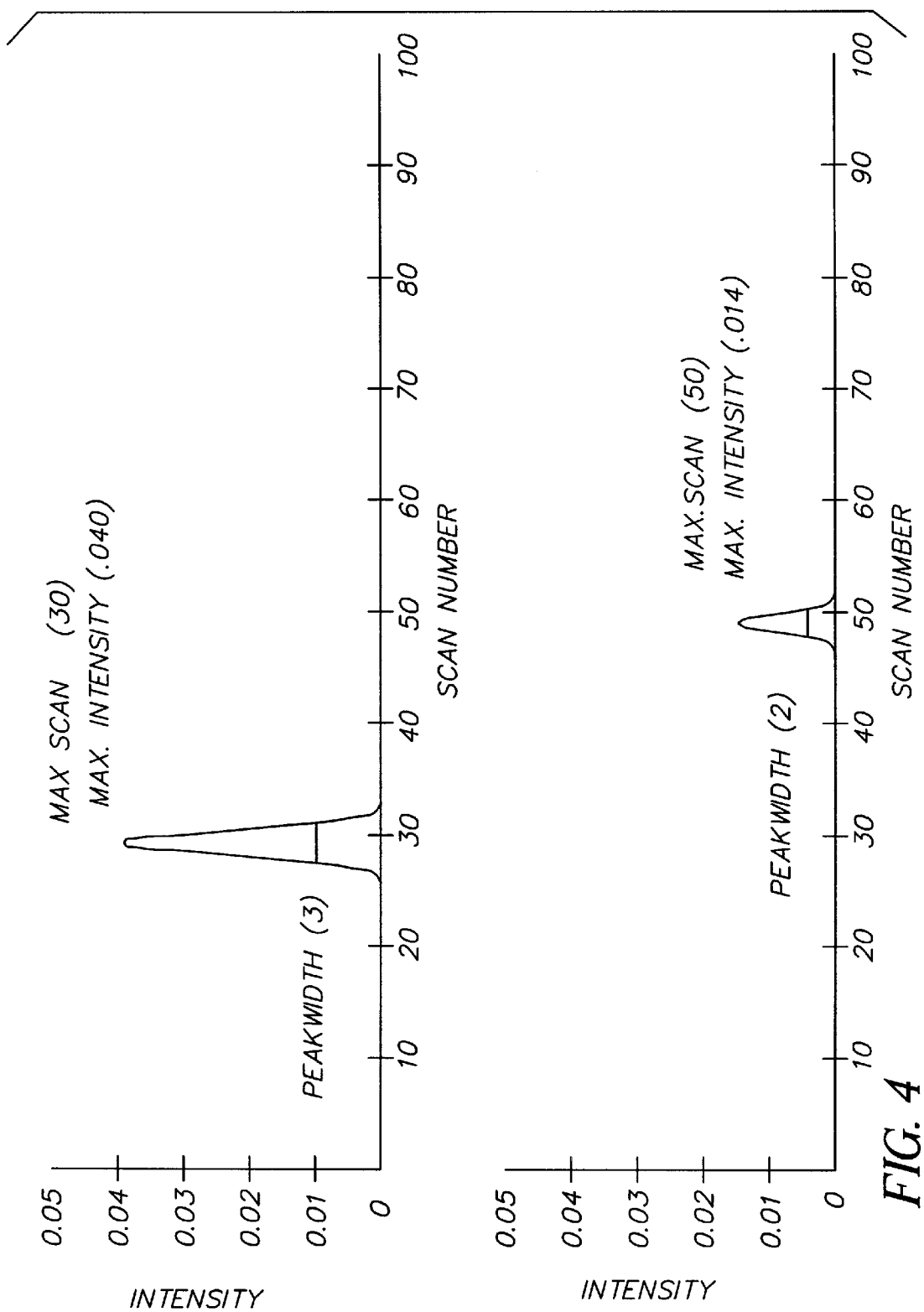
FIG. 4, several definitions are explained here. MAXSCAN the position of the maximum intensity in scan numbers, represented by the x-axis, MAXINT represents the intensity, represented by the y-axis, at MAXSCAN.

The principle object of the invention is to provide an improved method of qualitative and quantitative analysis for identifying and quantifying the chemical components of multiple samples of a complex mixture. Some of the terms used below are explained in FIG. 4.

The method comprises comparison and evaluation of the chemical components of multiple similar mixtures of organic chemicals comprising:

A first step of subjecting said organic material to chromatography to separate components of said mixture and a second step of subjecting the separated materials to mass spectrometry to detect and identify said components, wherein said chromatography and mass spectrometry is performed by a) injecting a sample onto a column;
b) separating components by partitioning at different rates in the column;
c) passing separated components into a mass spectrometer;
d) obtaining a series of spectra to detect all species present: and
e) storing the spectra of the samples in computer files; the improvement comprising enhancing the differences between the spectral data by a variable selection using the following steps:
   i) Calculate the mass chromatographic quality, MCQ, for each of the mass chromatograms in all files, for instance, using CODA (U.S. Pat. No. 5,672,869). Select the chromatograms which are above a certain minimum MCQ value in at one or more of the files. Instead of CODA, other data reduction methods can be used (B. E. Abbassi, H. Mestdagh and C. Rolando, Int. J. Mass Spectr. Ion. Proc., 141 (1995) 171–186) or by just reducing noise by using principal components analysis (T. A. Lee, L. M. Headly and J. K. Hardy, Anal. Chem., 63 (1991) 357–360).
   ii) selecting mass chromatograms for which at least one has a maximum intensity above a level of about 20 times the smallest intensity increase in the data to avoid noise and broad peaks.
   iii) selecting a difference of more than three in the scan position of any pair of the chromatograms and
   iv) ensuring that the ratio between intensities of peaks exceeds a factor of two in any pair of the chromatograms.

Figure 5A:
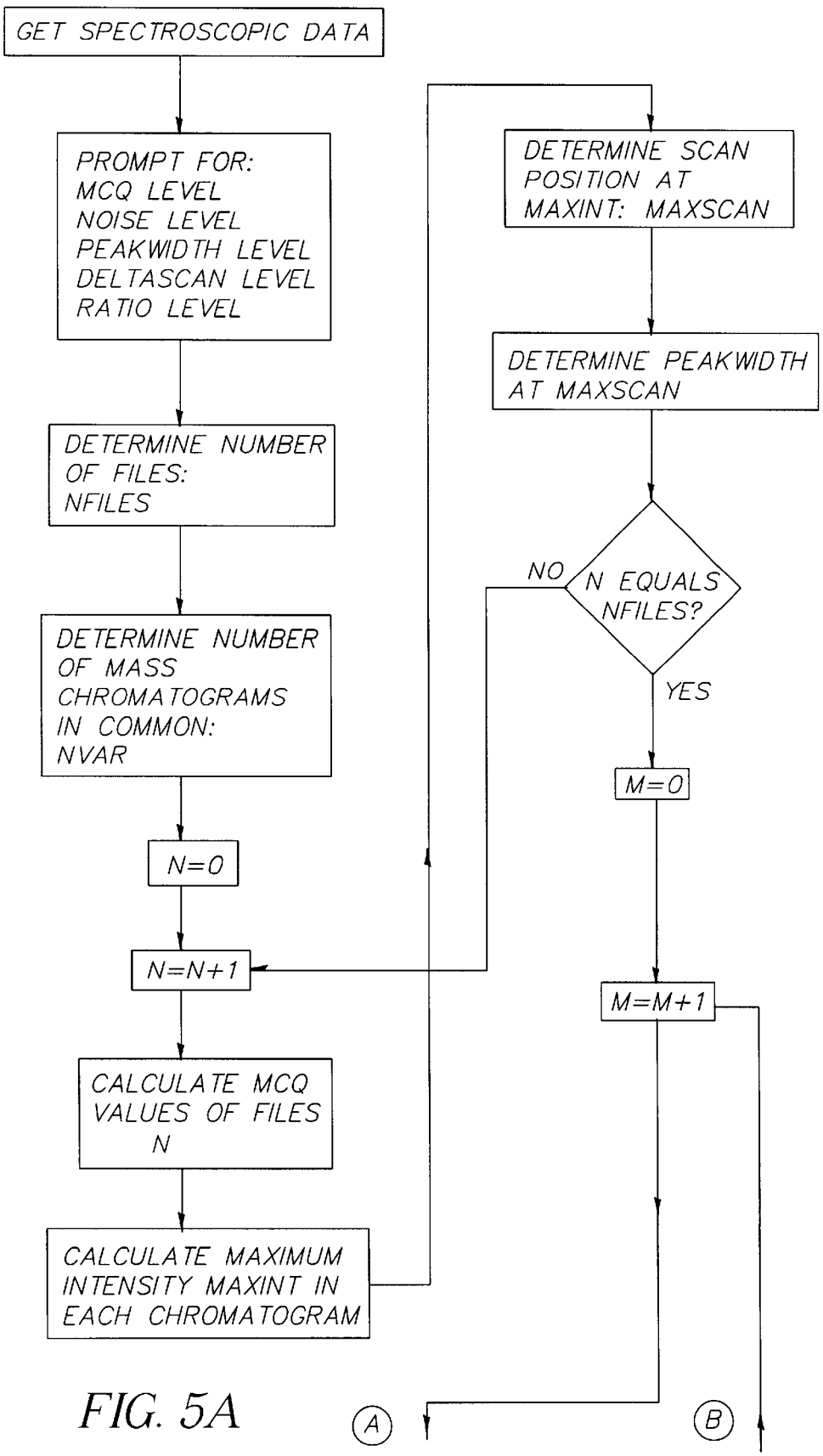
FIG. 5, flow diagram of COMPARELCMS.
Figure 5B:
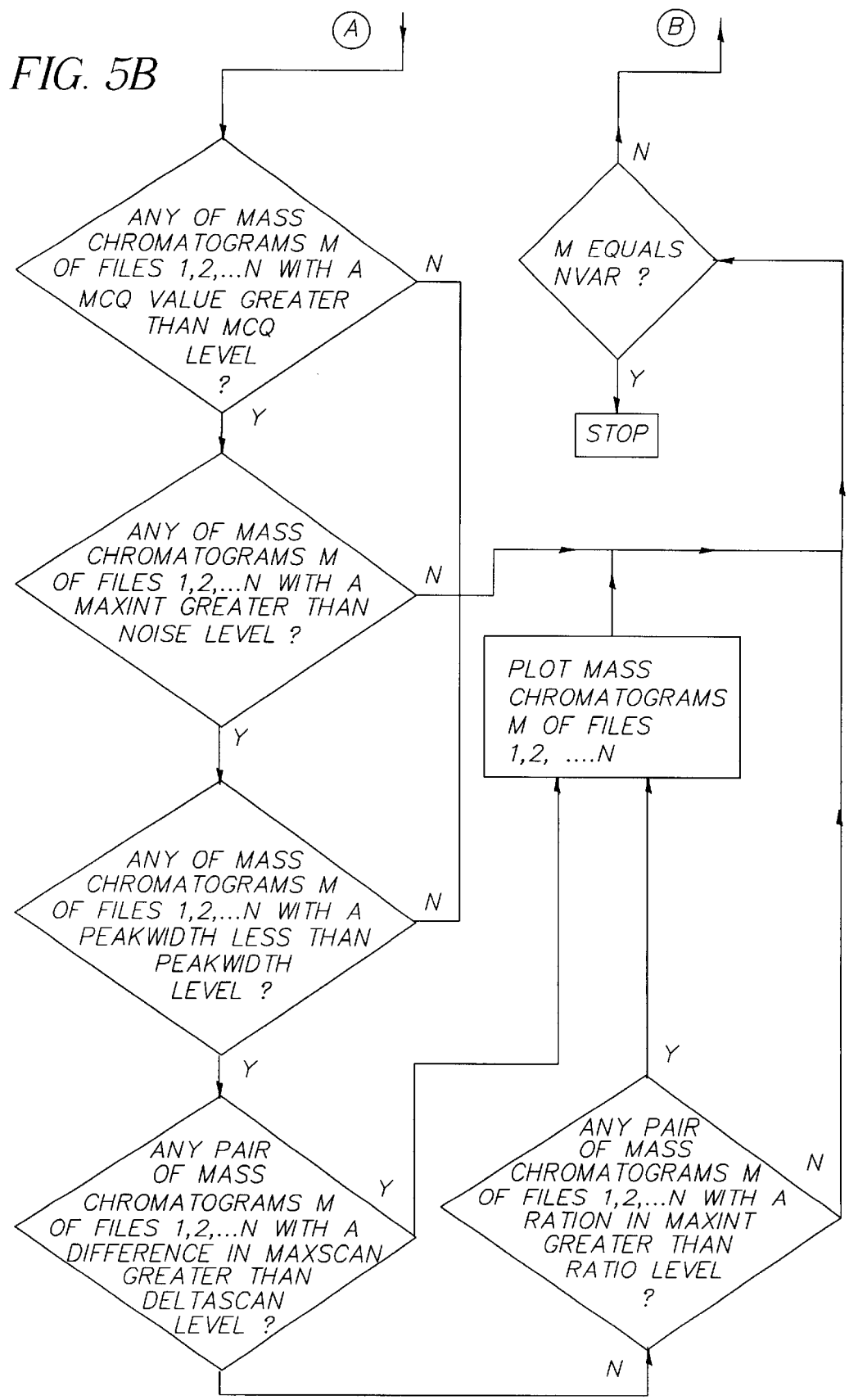

The flow diagram of the COMPARELCMS process is given in FIG. 5.

In a preferred embodiment, MCQ index in any of the chromatograms is at least 0.85, MAXINT in any of the chromatograms is at least 20 times the minimal intensity increase in the data, PEAKWIDTH in any of the chromatograms is less than 10 scans and the difference in MAXSCAN in any pair of chromatograms is more than three scans and the ratio of MAXINT in any pair of chromatograms is at least two.

The following example illustrates the method of analyzing data.

EXAMPLE

Mass Spectral Analysis

Figure 1A:
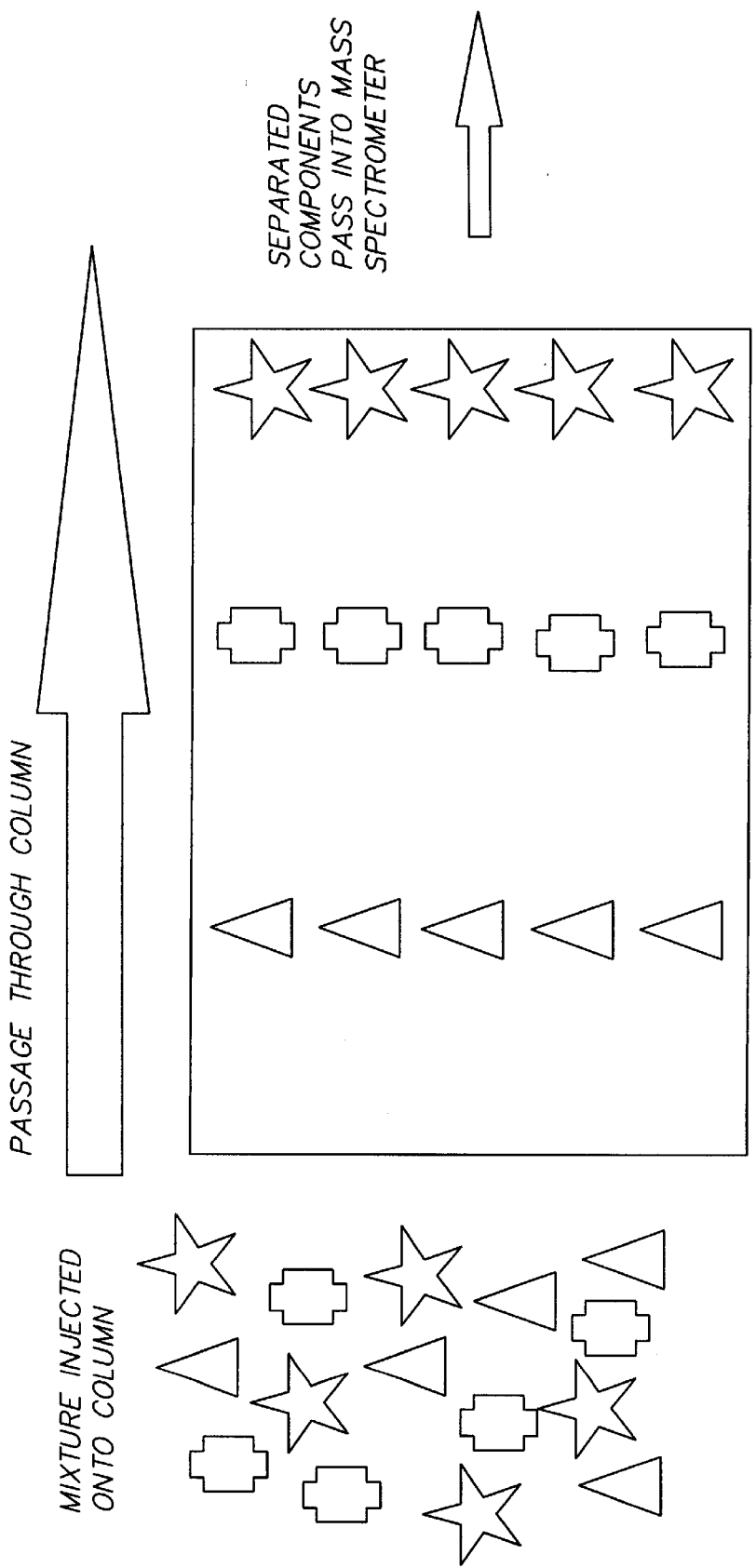
FIG. 1A is a schematic of a chromatographic separation of a three component mixture.
Figure 1B:
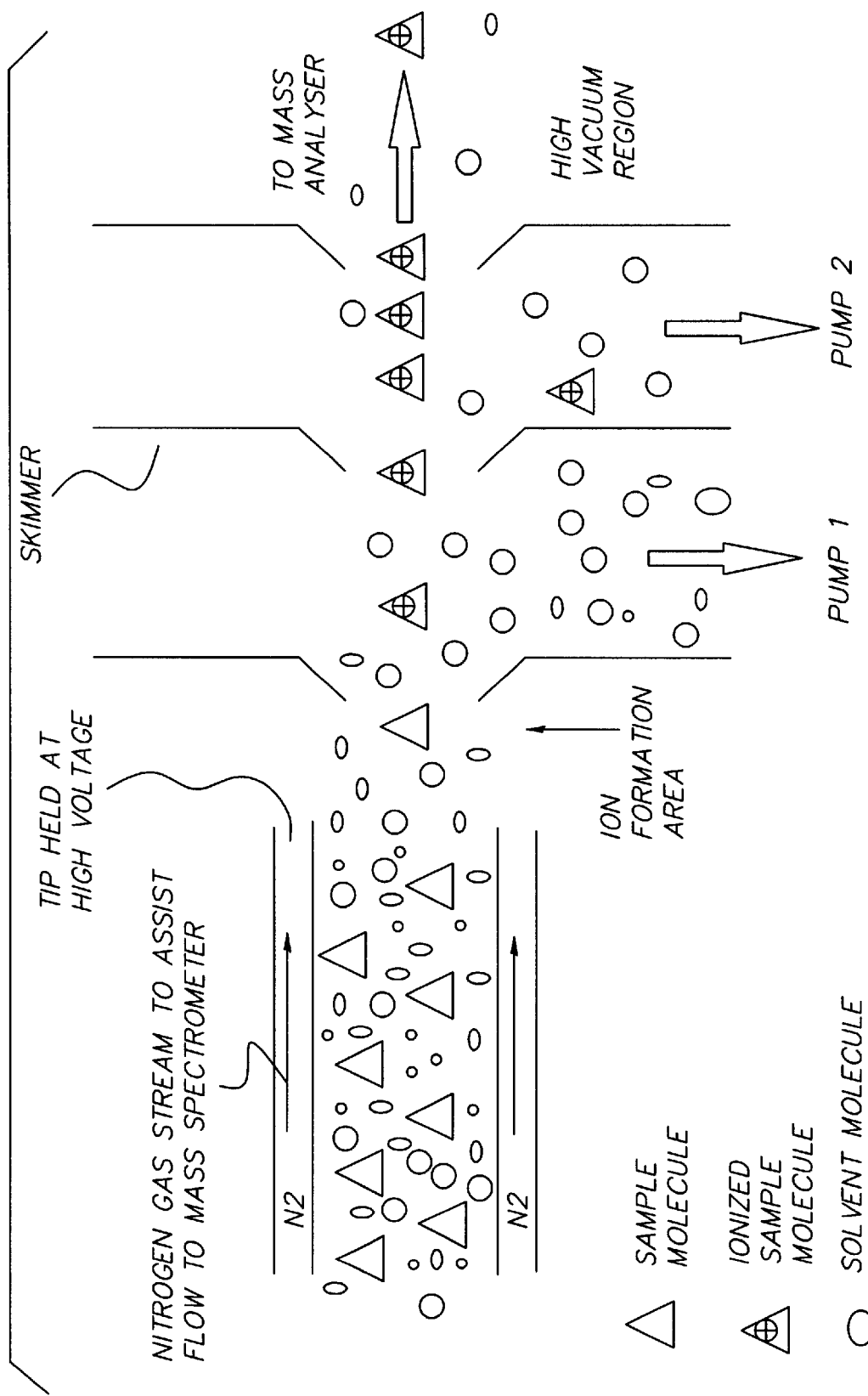
FIG. 1B is a schematic of an electrospray LC-MS interface.
Figure 2:
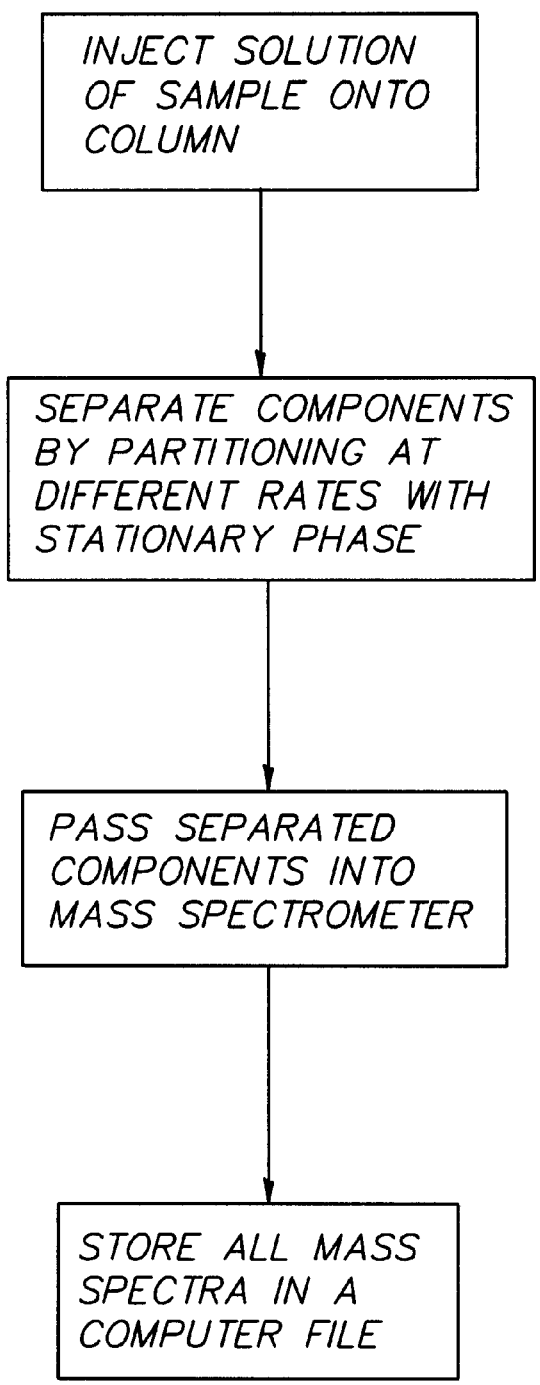
FIG. 2 is a flow diagram of chromatography with a spectrometric detector.
Figure 3:
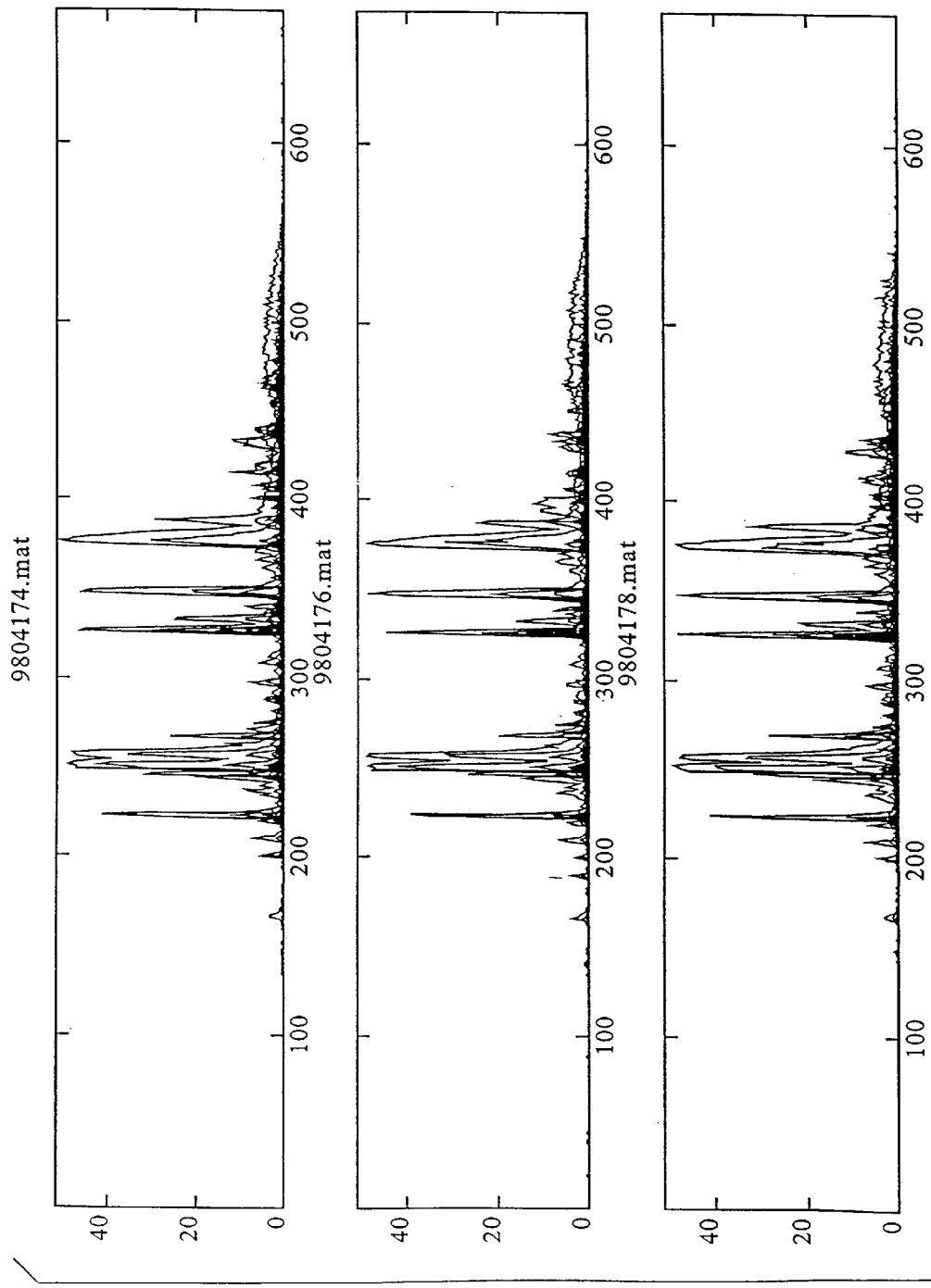
FIG. 3 shows the CODA reduced chromatograms of the three samples.
Figure 6:
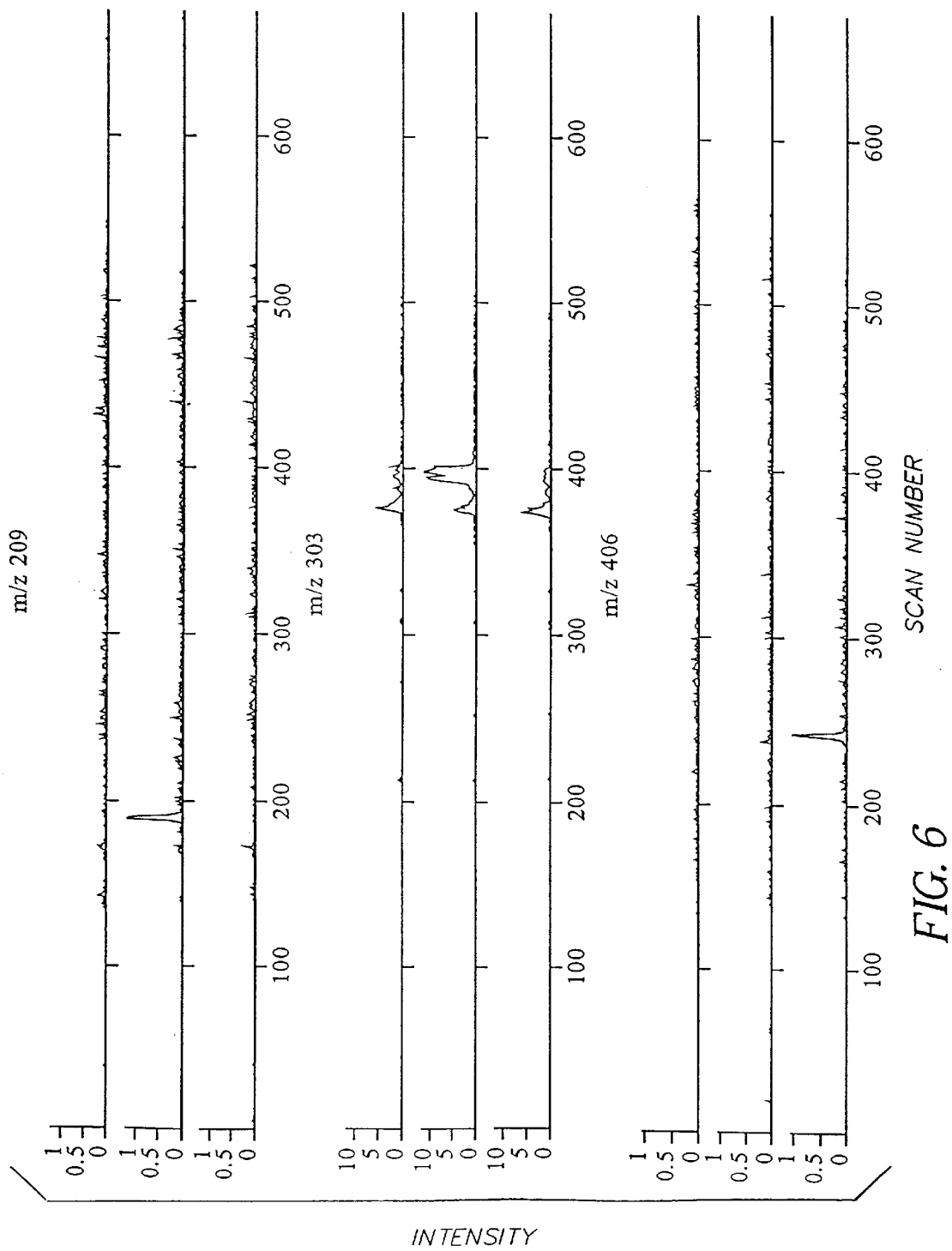
FIG. 6, three of the selected mass chromatograms selected by COMPARELCMS.

The LC-MS analysis was performed on a Sciex API 365 mass spectrometer coupled to a Hewlett Packard1050 liquid chromatograph via a Sciex Turbo Ion Spray interface. The mass analyzer is capable of scanning to 3000 daltons and a typical scan speed is 3 seconds for the entire mass range of a given experiment, although this is variable and occasionally will be changed to fit the needs of the experiment. This instrument is equipped with the Turbo Ion Spray LC/MS interface. The Turbo Ion Spray interface is a high flow rate (0.25 ml–1 ml/min), nebulization assisted Electrospray ionization source (See FIG. 1b). The Turbo Ion Spray interface is very robust. It consists of a hollow needle that the HPLC eluant is pumped through. No heat is involved. Instead a high voltage potential is placed on the needle and the sample is "sprayed" through it forming ions. This ionization process is called "Electro Spray" (ES) (Cole, R. Electrospray Ionization Mass Spectrometry: Fundamentals, Instrumentation, and Applications, Wiley: New York (1997)). The ions are formed in the Electro Spray process in an area that is at atmospheric pressure and are pulled through a skimmer, by electrical potential, into a region that is being pumped to remove the volatile solvents. This lowers the pressure and focuses the ions. The pressure is reduced further in another pumped region and, subsequently, the ions pass into the mass analyzer. There is no backpressure generated in the interface, which greatly simplifies interfacing to HPLC and other types of separations, such as ion chromatography and size exclusion chromatography. Maintenance is low and the instrument is easy to use. The instrument is automated and samples are analyzed overnight or over the weekend on a regular basis generating large amounts of data. The LC-MS chromatograms shown are extracts of three different lots of the same material. One of the lots exhibited poor performance, another showed some minor problems while the third performed well. The reduced CODA chromatograms are shown in FIG. 3 and a set of selected mass chromatograms from Comparelcms are shown in FIG. 6.

Data Analysis

The programs for this project were written in the development software MATLAB 5.2.1.1420 (The MathWorks, Inc., Cochituate Place, 24 Prime Park Way, Natich, Mass. 01760). The computer configuration is a PENTIUM, 266 MHZ, 128 MB of RAM.

Three highly similar samples were analyzed by LC/MS. From the measured data, a quality index is calculated with the previously described CODA. The index is called the MCQ (mass chromatographic quality) index. The MCQ has a value between 0 and 1. The higher the number the higher the quality of the data. In the example shown below, the MCQ index used is 0.85 for a smoothing window of 3 (in the original CODA patent the window was introduced as a variable, in practice it appeared that a constant value of 3 is appropriate). For the files used, this reduces the number of chromatograms significantly, see Table I. In FIG. 3 the CODA reduced data of the three related samples are shown. The problems with LC-MS of closely related samples are clearly illustrated; it is difficult to determine the small differences by simple visual evaluation.

The selected mass chromatograms of the three files were combined. Due to the high overlap, this results in a total of 191 mass chromatograms, see Table I. In order to reduce the number of mass chromatograms further, only the mass chromatograms above a certain minimum level are kept. In the example, the noise is 20 times the digitization step of the instrument. Furthermore, very broad peaks are often not of interest to the researcher. In the example shown, peaks of less than 10 scans wide at 0.25 of the peak height are discarded. The value 0.25 of the peak height was chosen since broad peaks are often very noisy, and the more commonly used value 0.5 of the peak height did not perform well. The use of these two criteria reduced the number of peaks from 191 to 146. Of these mass chromatograms, ONLY the ones that are different are of interest. Therefore, only mass chromatograms are selected which have:

a) A different scan position, i.e. the maximum difference value of MAXSCAN (see FIG. 4) of the mass chromatograms should be more than 3 scans (in this example). If it is less than 3 scans, the peaks are considered to have an identical scan position. OR b) The maximum difference in the peak intensities MAXINT should be more than 5 (in this example).

This reduces the number of mass chromatograms to 41. This shows that COMPARELCMS reduces the number of mass chromatograms very significantly. Compared to the original number of mass chromatograms, the data is reduced by a factor of 50; compared to the CODA results, the data is reduced by a factor of 5.

In order to facilitate comparison of the selected chromatograms, plots are generated of the chromatograms, selected because of differences, simultaneously. This is a time saving step compared to the current tools, where the mass chromatograms of only one file can be plotted. An example of the 3 selected chromatograms is presented in FIG. 6. Note that the intensities of some of these mass chromatograms is about 2% of the intensities displayed in FIG. 3. The manual evaluation to select chromatograms of this file cost 4 hours, while the use of COMPARELCMS results in obtaining the same results in less than 5 minutes.

TABLE 1

|  | Original | CODA | Combined | Deleting low intensity and broad chromatograms | Selecting dissimilar chromatograms |
|---|---|---|---|---|---|
| Sample 1 | 1938 | 146 | | | |
| Sample 2 | 1937 | 138 | 191 | 146 | 41 |
| Sample 3 | 1940 | 160 | | | |

While the invention has been described with particular reference to a preferred embodiment, it will be understood by those skilled in the art the various changes can be made and equivalents may be substituted for elements of the preferred embodiment without departing from the scope of the invention. In addition, many modifications may be made to adapt a particular situation in material to a teaching of the invention without departing from the essential teachings of the present invention.

What is claimed is:

1. A method of identifying and quantifying the chemical components of a mixture of organic materials comprising: a first step of subjecting said organic material to chromatography to separate components of said mixture and a second step of subjecting the separated materials to spectrometry to detect and identify said components, wherein said chromatography and spectrometry is performed by
   a) injecting a sample into a column;
   b) separating components by partitioning at different rates in the column;
   c) passing separated components into a spectrometer;
   d) obtaining a series of spectra to detect all species present; and
   e) storing the spectra in a computer file and reducing the number of mass chromatograms; the improvement comprising enhancing the spectral data by a variable selection using the following steps:
      i) selecting mass chromatograms for which at least one has an MCQ level above a certain level;
      ii) selecting mass chromatograms for which at least one has a maximum intensity above a level of about 20 times the smallest intensity increase in the data to avoid noise and broad peaks;
      iii) selecting a difference of more than three in the scan position of any pair of the chromatograms; and
      iv) ensuring that the ratio between intensities of peaks exceeds a factor of two in any pair of the chromatograms.

2. The method of claim 1 wherein steps i), ii), iii) and iii) comprise;
   a) Determining the MCQ values by CODA;
   b) Determining the maximum intensity MAXINT for each of the mass chromatograms in all files;
   c) Determining scan position MAXSCAN at MAXINT for each of the mass chromatograms in all files;
   d) Determining with of peak PEAKWIDTH of the peak at MAXSCAN for each of the mass chromatograms in all files;
   e) For every mass, plot the mass chromatograms of each file when:
      a.) any MCQ value is larger than predefined value AND
      b.) any MAXINT is larger than a predefined noise level AND
      c.) any PEAKWIDTH is less than predefined level AND
      d.) any difference in MAXSCAN is greater than predefined level OR
         any pair of MAXINT values having a ratio larger than a predefined level.

3. The method of claim 2 wherein MCQ in any of the chromatograms is at least 0.85 MAXINT in any of the chromatograms is at least 20 times the minimal intensity increase in the data, PEAKWIDTH in any of the chromatograms is less than 10 scans and the difference in MAXSCAN in any pair of chromatograms is more than three scans and the ratio of MAXINT in any pair of chromatograms is at least two.

4. The method of claim 1 wherein the chromatography is liquid chromatography.

5. The method of claim 1 wherein the spectrometry is mass spectrometry.

6. The method of claim 1 wherein the chromatography is gas chromatography and the spectrometry is mass spectrometry.

7. The method of claim 1 wherein the chromatography is liquid chromatography and the spectroscopy is UV spectroscopy.

8. The method of claim 1 wherein the chromatography is liquid chromatography and the spectroscopy is NMR spectroscopy.

* * * * *